US011941026B2

(12) United States Patent
Preston et al.

(10) Patent No.: US 11,941,026 B2
(45) Date of Patent: Mar. 26, 2024

(54) SYSTEM AND METHOD FOR SYNCING ASYNCHRONOUSLY RECEIVED SEQUENTIAL DATA FROM DISPARATE SOURCES

(71) Applicant: HealthSnap, Inc., Miami, FL (US)

(72) Inventors: Chase Preston, Miami, FL (US); Yenvy Truong, Lighthouse Point, FL (US)

(73) Assignee: HealthSnap, Inc., Miami, FL (US)

( * ) Notice: Subject to any disclaimer, the term of this patent is extended or adjusted under 35 U.S.C. 154(b) by 30 days.

(21) Appl. No.: 17/139,534

(22) Filed: Dec. 31, 2020

(65) Prior Publication Data

US 2021/0209130 A1 Jul. 8, 2021

Related U.S. Application Data

(60) Provisional application No. 62/956,918, filed on Jan. 3, 2020.

(51) Int. Cl.
*G06F 16/00* (2019.01)
*G06F 16/25* (2019.01)
(Continued)

(52) U.S. Cl.
CPC .......... *G06F 16/273* (2019.01); *G06F 16/258* (2019.01); *G06F 16/285* (2019.01); *G16H 10/60* (2018.01); *H04L 67/1095* (2013.01)

(58) Field of Classification Search
CPC .... G06F 16/273; G06F 16/258; G06F 16/285; G06F 2201/835; G16H 10/60; H04L 67/1095
See application file for complete search history.

(56) References Cited

U.S. PATENT DOCUMENTS 11,017,058 B1 * 5/2021 McDavid-Arno ...................... G06F 16/2237
2011/0288877 A1 * 11/2011 Ofek ...................... G16H 50/20 707/661

(Continued)

FOREIGN PATENT DOCUMENTS

JP 2010176615 A * 8/2010
JP 5245873 B2 * 7/2013

OTHER PUBLICATIONS

Kakria et al., "A Real-Time Health Monitoring System for Remote Cardiac Patients Using Smartphone and Wareable Sensors", Hiindawi Publishing Corporation, vol. 2015, Article ID 373474, pp. 1-11 (Year: 2015).*

*Primary Examiner* — Alexander Khong
(74) *Attorney, Agent, or Firm* — Sterne, Kessler, Goldstein Fox P.L.L.C.

(57) ABSTRACT

Described herein is a system for syncing asynchronously received sequential data from disparate sources. In an embodiment, a central system may receive data transmissions from disparate sources. Each data transmission includes a timestamp and an identifier of the disparate source. The central system may sort the data from the data transmissions of disparate sources in chronological order based on the timestamps. The central system may group the data based on the identifier of the disparate source and normalize the data of the data transmissions to be in a specified format. The central system may store the normalized data of the data transmission in a data storage facility based on the identifier of the disparate source and the sorted order of the data.

21 Claims, 8 Drawing Sheets

(51) Int. Cl.
*G06F 16/27* (2019.01)
*G06F 16/28* (2019.01)
*G16H 10/60* (2018.01)
*H04L 67/1095* (2022.01)

(56) References Cited

U.S. PATENT DOCUMENTS

| | | | | |
|---|---|---|---|---|
| 2012/0215560 | A1* | 8/2012 | Ofek | G16H 10/00 |
| | | | | 705/3 |
| 2015/0302441 | A1* | 10/2015 | Katsuyama | G06Q 30/0206 |
| | | | | 705/36 R |
| 2019/0020465 | A1* | 1/2019 | Carlstedt | H04L 43/106 |
| 2019/0333165 | A1* | 10/2019 | Lyle | G06Q 50/04 |

* cited by examiner

FIG. 3

SYSTEM AND METHOD FOR SYNCING ASYNCHRONOUSLY RECEIVED SEQUENTIAL DATA FROM DISPARATE SOURCES

CROSS-REFERENCE TO RELATED APPLICATIONS

This application claims priority to U.S. Provisional Patent Application No. 62/956,918, filed on Jan. 3, 2020, the contents of which are incorporated herein by reference in their entirety.

BACKGROUND

Systems may be communicatively coupled to disparate sources, which in turn continuously or periodically collect or receive information. The disparate sources may transmit large amounts of this collected data to a system, often at times later than the data was initially collected. For example, the disparate sources may receive a request to transmit the data to a centralized system on a given date or time that is different than when the system receives the data. Further, different disparate sources may transmit data to the centralized system at different times or covering different time periods. For example, the disparate sources may be smart devices connected to the centralized system through a network. The disparate sources may receive a request to transmit data to the system or may be scheduled to transmit data periodically. However, the disparate source may lose network connectivity, and transmitting the data may be delayed until network connectivity is restored. Or, a given disparate source may be scheduled to routinely transmit data asynchronously with other disparate sources, even if the data collection time periods covered by the disparate sources overlap. This causes the centralized system to receive data that is out of order in terms of dates and times that the data was intended to be transmitted. Furthermore, conventional systems operate based on a time or date of receipt. This can cause the centralized system to improperly process data based on an incorrect mapping between receipt date and creation date. Improperly processing data can cause the system to process data inaccurately, leading to system inefficiencies and possible system failures.

BRIEF DESCRIPTION OF THE DRAWINGS

The accompanying drawings, which are incorporated herein and form a part of the specification, illustrate the embodiments of the present disclosure, and together with the description, further serve to explain the principles of the embodiments and enable a person skilled in the pertinent art to make and use the embodiments, individually, or as a combination thereof.

FIG. 3 is an example data transmission calendar GUI indicating a patient's data transmission information over several months according to an example embodiment.

In the drawings, like reference numbers generally indicate identical or similar elements. Additionally, generally, the left-most digit(s) of a reference number identifies the drawing in which the reference number first appears.

DETAILED DESCRIPTION

Described herein is a system for syncing asynchronously received sequential data from disparate sources. As described above, a system may asynchronously receive large amounts of sequential data from disparate sources. The system may receive data from various data sources at various dates and times. The dates and times of receipt may not correspond with the date and time the disparate source may have attempted to originally transmit the data or with the date and time the disparate source generated, collected, or received the data itself.

In an embodiment, a central system may receive data transmissions from disparate sources. Each data transmission includes one or more timestamps and an identifier of the disparate source. In an embodiment, the timestamp corresponds to the transmission as a whole and reflects the time that a data transmission was attempted to be transmitted by a disparate source. In another embodiment, there are multiple timestamps in a data transmission, each timestamp corresponding to the time that a data element was generated, collected, or received by the disparate data source. The central system may sort the data transmissions in chronological order based on the timestamp(s). The central system may group the data transmissions based on the identifiers of the disparate sources and normalize data in the data transmissions to be in a specified format. The central system may store the normalized data of the data transmissions in a data storage facility based on the identifiers of the disparate sources.

By sorting and grouping the data transmissions based on the timestamp and the disparate source identifier, the system is able to ensure that the central system may process the data accurately. By doing so, the system avoids inefficiencies and potential system failures caused by processing invalid data.

While the below figures describe this data syncing method in the context of receiving health-related data at a healthcare provider's electronic system from a disparate source such as a health monitoring device, it should be understood that the data syncing method described herein can be used in a number of different applications where sequential data is received asynchronously at a central system from disparate data sources, such as smart home devices, laboratory sensors, instrumentation sensors, etc.

Figure 1:
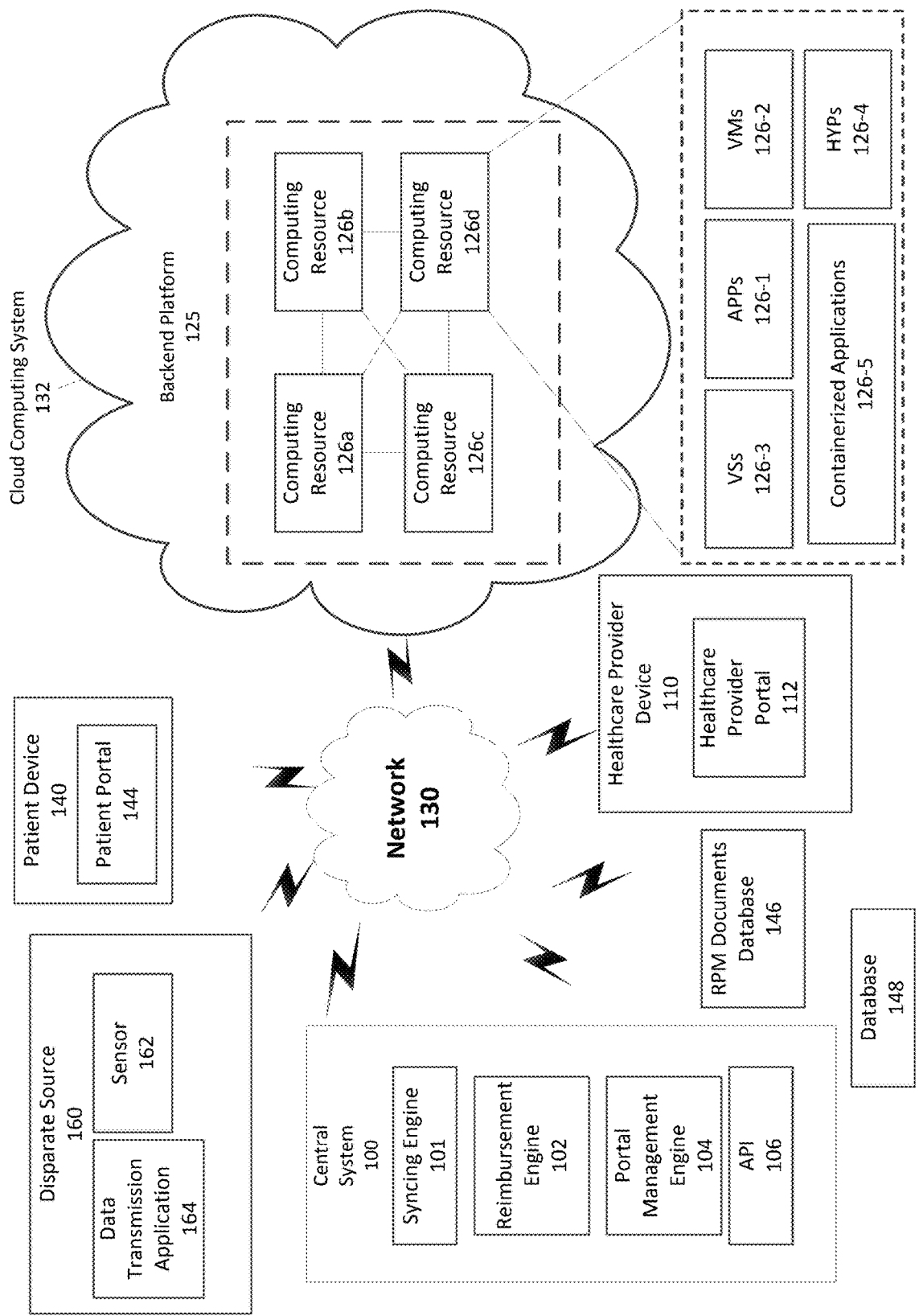
FIG. 1 is a block diagram of an example environment in which systems and/or methods described herein may be implemented according to an example embodiment.

FIG. 1 is a block diagram of an example environment in which systems and/or methods described herein may be implemented. The environment may include a central system 100, a healthcare provider device 110, a patient device 140, a remote patient monitoring ("RPM") documents database 146, a database 148, a backend platform 125, a cloud computing environment 132, multiple disparate sources 160, and a network 130. The devices within the environment may be connected through wired connections, wireless connections, or a combination of wired and wireless connections. Central system 100 may reside fully or partially on the cloud computing system 132 or may be a standalone system. The central system may include a syncing engine 101, a reimbursement engine 102, and portal management engine 104. Central system 100 may further include an API 106. The API may be configured to interface with healthcare provider device 110, patient device 140, and disparate sources 160. Patient device 140 may include a portal 144. Healthcare provider device 110 may include a healthcare provider portal 112. Portal 144 and the healthcare provider portal 112 may be websites or executable applications configured to interface with central system 100.

A disparate source 160 may be a wearable device coupled to a wrist strap, watch, glasses, headband, waistband, and/or the like, or a smart device such as a smartphone or tablet. A disparate source 160 may also be an application executing on a smart device, where the application gathers its own data. Disparate source 160 may include a sensor 162 to measure data for a user and a data transmission application 164. Data transmission application 164 may interface with central system 100. Sensor 162 may sense, track, and store the measured data for a user. This sensing, tracking, and storing may occur continuously or periodically. Data transmission application 164 may extract the data from sensor 162. Data transmission application 164 may extract the data from sensor 162 after a specified amount of time, at intervals, or on the detection of new data being sensed and stored. The data may be health data, including, for example, weight, blood pressure, pulse oximetry, respiratory flow rate, and/or the like.

In an embodiment, data collection device 162 may be coupled to patient device 140. Once coupled to patient device 140, portal 144 may pull the data from sensor 162. Alternatively, data collection device 162 may operate independently from patient device 140.

In an example embodiment, one or more portions of network 130 may be an ad hoc network, an intranet, an extranet, a virtual private network (VPN), a local area network (LAN), a wireless LAN (WLAN), a wide area network (WAN), a wireless wide area network (WWAN), a metropolitan area network (MAN), a portion of the Internet, a portion of the Public Switched Telephone Network (PSTN), a cellular telephone network, a wireless network, a WiFi network, a WiMax network, any other type of network, or a combination of two or more such networks.

Backend platform 125 may include a server or a group of servers. In an embodiment, backend platform 125 may be hosted in a cloud computing environment 132. It may be appreciated that backend platform 125 may not be cloud-based or may be partially cloud-based. Central system 100 may include one or more devices configured to interface with backend platform 125.

Cloud computing environment 132 includes an environment that delivers computing as a service, whereby shared resources, services, etc., may be provided to backend platform 125. Cloud computing environment 132 may provide computation, software, data access, storage, and/or other services that do not require end-user knowledge of a physical location and configuration of a system and/or a device that delivers the services. The cloud computing system 132 may include computer resources 126a-d.

Each computing resource 126a-d includes one or more personal computers, workstations, computers, server devices, or other types of computation and/or communication devices. The computing resource(s) 126a-d may host backend platform 125. The cloud resources may include compute instances executing in the computing resources 126a-d. The computing resources 126a-d may communicate with other computing resources 126a-d by wired connections, wireless connections, or a combination of wired or wireless connections.

Computing resources 126a-d may include a group of cloud resources, such as one or more applications ("APPs") 126-1, one or more virtual machines ("VMs") 126-2, virtualized storage ("VS") 126-3, one or more hypervisors ("HYPs") 126-4, and one or more containerized applications 126-5.

Application 126-1 may include one or more software applications that may be provided to or accessed by central system 100. Alternatively, the application 126-1 may eliminate a need to install and execute software applications on patient device 140 or healthcare provider device 110. The application 126-1 may include software associated with backend platform 125 and/or any other software configured to be provided across cloud computing environment 132. The application 126-1 may send/receive information from one or more other applications 126-1 by the virtual machine 126-2.

Virtual machine 126-2 may include a software implementation of a machine (e.g., a computer) that executes programs like a physical machine. Virtual machine 126-2 may be either a system virtual machine or a process virtual machine, depending upon the use and degree of correspondence to any real machine by virtual machine 126-2. A system virtual machine may provide a complete system platform that supports execution of a complete operating system (OS). A process virtual machine may execute a single program and may support a single process. The virtual machine 126-2 may execute on behalf of a user and/or on behalf of one or more other backend platforms 125 and may manage the infrastructure of cloud computing environment 132, such as data management, synchronization, or long-duration data transfers.

Virtualized storage 126-3 may include one or more storage systems and/or one or more devices that use virtualization techniques within the storage systems or devices of computing resource 126a-d. With respect to a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how administrators manage storage for end users. File virtualization may eliminate dependencies between data accessed at a file-level and the location where files are physically stored. This may enable optimization of storage use, server consolidation, and/or performance of non-disruptive file migrations.

Hypervisor 126-4 may provide hardware virtualization techniques that allow multiple operations systems (e.g., "guest operating systems") to execute concurrently on a host computer, such as computing resource 126a-d. Hypervisor 126-4 may present a virtual operating platform to the guest operating systems and may manage the execution of the guest operating systems multiple instances of a variety of operating systems and may share virtualized hardware resources.

Containerized applications 126-5 may provide for executing distributed applications without having to launch a VM for each distributed application. Containerized applications 126-5 may be implemented by deploying virtualized application containers on a common OS using a platform. As a non-limiting example, the platform may be a platform provided Docker Inc., of San Francisco, CA.

In an embodiment, disparate source 160 may execute the data transmission application 164. Data transmission application 164 may extract/pull data from sensor 162 of disparate source 160. As an example, data transmission application 164 may extract/pull the data every 24 hours. Data transmission application 164 may generate a data transmission, including the data pulled from sensor 162. Data transmission application 164 may attempt to transmit the data transmission from disparate source 160 to central system 100. In response to attempting to transmit the data transmission from disparate source 160 to the central system, data transmission application 164 may embed a timestamp indicating the date and time of the attempted data transmission and a disparate source identifier in the data transmission. Additionally or alternatively, a timestamp may be added to or may be already associated with each data element within the data transmission based on a time that the data was generated, collected, or received by sensor 162. In an embodiment, data transmission application 164 may automatically transmit the data transmission to central system 100 after collecting a specified amount of data.

API 106 may receive the data transmission from the data transmission application 164. Each of the data transmissions may include one or more timestamps and a disparate source identifier. API 106 may receive data transmissions from multiple different disparate sources. Each disparate source may be associated with the same or a different user. Additionally, API 106 may receive multiple data transmissions from the same disparate source 160 of a single user.

Syncing engine 101 may determine whether the data included in the data transmission is in a correct format. For example, the health data may be received in JavaScript Object Notation (JSON) data-interchange format or eXtensible Markup Language (XML) format. Syncing engine 101 may determine whether the received format is acceptable by database 148. In the event the data is not in the correct format, syncing engine 101 may normalize the data into a format accepted by database 148. The data transmission may include a disparate source ID from which the data transmission was transmitted. Syncing engine 101 may identify the user of disparate source 160 using the disparate source ID. For example, the syncing engine 102 may correlate the disparate source ID in the data transmission with the disparate source ID of disparate source 160 tied to the patient. Syncing engine 101 may store the data in database 148 as correlated to the patient's records.

Syncing engine 101 may determine a date and time corresponding to the data in the data transmission from disparate source 160 based on the timestamp. As an example, a disparate source 160 may not transmit (e.g., may attempt and fail to transmit) a data transmission as scheduled when disparate source 160 has limited network connectivity (e.g., during airplane travel), such that the data transmission is not completed until a later date. Syncing engine 101 may determine the appropriate time or date to ascribe to the data based on the timestamp so that the data transmission is accounted for the day disparate source 160 generated, collected, or received the data, or made an attempt to send the data, rather than the day when the data transmission was actually completed. The data may be stored in database 148, based on the time stamp and the disparate source ID.

As described above, central system 100 may asynchronously receive sequential data transmissions from multiple different disparate sources 160. Central system 100 may receive large amounts of data transmissions simultaneously from disparate sources 160. Instead of maintaining the data in order of receipt, syncing engine 101 may sort the data transmissions in chronological order of the time stamp. Syncing engine 101 may group the data transmissions based on the disparate source ID so that the data transmissions received from a given disparate source 160 are grouped and chronologically ordered with regards to other disparate sources 160. The data included in the data transmissions may be stored in database 148 based on the disparate source ID and the chronological order of the data transmission.

As a non-limiting example, central system 100 may receive the following data transmissions:

| Data transmission 1 |
|---|
| Timestamp: Jan. 12, 2017 5:56:30<br>Disparate source ID: 123 |
| Data transmission 2 |
| Time stamp: Jan. 1, 2017 12:28:30<br>Disparate source ID: 124 |
| Data transmission 3 |
| Timestamp: Jan. 5, 2017 6:23:12<br>Disparate source ID: 123 |
| Data transmission 4 |
| Timestamp: Jan. 2, 2017 10:44:36<br>Disparate source ID: 567 |

Syncing engine 101 may sort the data transmissions as follows:

| Data transmission 2 |
|---|
| Time stamp: Jan. 1, 2017 12:28:30<br>Disparate source ID: 124 |
| Data transmission 4 |
| Timestamp: Jan. 2, 2017 10:44:36<br>Disparate source ID: 567 |
| Data transmission 3 |
| Timestamp: Jan. 5, 2017 6:23:12<br>Disparate source ID: 123 |
| Data transmission 1 |
| Time stamp: Jan. 12, 2017 5:56:30<br>Disparate source ID: 123 |

Syncing engine 101 may group the data transmissions as follows:

| Disparate source ID: 123 |
|---|
| Data transmission 3 |
| Time stamp: Jan. 5, 2017 6:23:12<br>Data transmission 1 |
| Time stamp: Jan. 12, 2017 5:56:30 |

| |
|---|
| Disparate source ID: 567 |
| Data transmission 4 |
| Time stamp: Jan. 2, 2017 10:44:36 |
| Disparate source ID: 124 |
| Data transmission 2 |
| Time stamp: Jan. 1, 2017 12:28:30 |

Based on the above table, the data transmissions are accounted for the disparate source from which they were transmitted and are accounted for by the timestamp associated with the data, rather than the time of receipt of the data.

As a non-limiting example, the system for asynchronously syncing received sequential data received from disparate sources may be implemented for remote patient monitoring (RPM). RPM is the ability for a healthcare provider to remotely monitor their patient's physiological data. By providing an RPM service, a healthcare provider is able to submit reimbursement requests to The Centers for Medicare & Medicaid Services (CMS). For example, a healthcare provider may request reimbursement for the following reimbursement codes: a set up reimbursement (code: 99453), a data transmission reimbursement (code: 99454), and a treatment reimbursement (code: 99457 & 99458).

A healthcare provider may be eligible for a set up reimbursement based on remote monitoring of physiologic parameter(s) (e.g., weight, blood pressure, pulse oximetry, respiratory flow rate), and specifically for initial set-up and patient education regarding the use of equipment. The set up reimbursement may require setting up a patient in an RPM program and confirming that they are connected, they have a device that they can connect to the RPM program, and data is streaming.

A healthcare provider may be eligible for a data transmission reimbursement based on continued remote monitoring of physiologic parameter(s) (e.g., weight, blood pressure, pulse oximetry, respiratory flow rate). Specifically, the reimbursement may be awarded based on the healthcare provider receiving a certain number of data transmissions through the RPM program over a given period of time, such as 30 days, 1 month, 6 months, and/or the like. The data transmission reimbursement may require a patient transmitting data, including health data about the patient, for a minimum number of days within a specified time window (e.g., 16 out of every 30 days) and after a specified amount of days have passed since the last triggered data transmission reimbursement eligibility or since the date of enrollment.

A healthcare provider may be eligible for a treatment reimbursement based on remote physiologic monitoring treatment management services, including a certain number of minutes of clinical staff/physician/other qualified healthcare professional time in a given time period, such as 20 or more minutes per calendar month. The treatment reimbursement may require interactive communication with the patient/caregiver during the time period over a minimum threshold number of days within a given time window and after a specified number of days have passed since the last triggered data transmission reimbursement eligibility or since the date of enrollment. For example, treatment reimbursement may require interactive communication with the patient/caregiver during the time period and data transmission reimbursement eligibility.

An example implementation use case follows, based on the architecture of FIG. 1, according to an embodiment of the invention. A healthcare provider may execute the healthcare provider portal 112 using healthcare provider device 110. The healthcare provider portal 112 may provide the healthcare provider information. The healthcare provider portal 112 may provide the ability to generate and transmit RPM enrollment invitations to patients. The healthcare provider portal 112 may provide a selection of data that the healthcare provider would like to monitor for the patient. The data may be one or more of, for example, and without limitation, body weight, height, body fat, resting heart rate, blood pressure, VO2max, and/or the like. Prior to sending the invitation, the healthcare provider portal 112 may prompt the healthcare provider to provide various types of information such as a medically-necessary RPM enrollment reason, a diagnosis, and an ordering provider. Such information may be input via a variety of interface features such as a dropdown menu containing prepopulated selections, a free input box, radio buttons, and/or the like. The ordering provider may be entered, for example, using a dropdown menu of provider names. In an embodiment, the healthcare provider may upload a comma-separated values (CSV) file, including information about the patient(s) to be invited. The patient name, contact information, reason for RPM enrollment, and diagnosis may be extracted from the CSV file and auto-populated into input boxes and dropdown menus. The invitation may be sent to the patient in an email, including a link or Short Messaging Service (SMS) message, including a link.

Once a patient is invited to enroll in RPM, a patient's profile page may be generated on the healthcare provider portal 112, along with an associated status. For example, the healthcare provider portal 112 may render the RPM status as "Pending" on the patient profile page. An activity may be created for "RPM enrollment pending". The healthcare provider may send reminders to the patient or cancel the invitation using the healthcare provider portal 112. The patient profile page may also include a section for RPM documents to be stored. RPM documents may include documentation containing, for example, reasons for RPM enrollment, diagnoses, insurance information, consent forms, and/or the like. The patient profile page may also include information about the patient's connected disparate source 160. The healthcare provider portal 112 may provide to the healthcare provider a patient list, including enrolled, invited, and pending patients.

In response to launching the patient portal 144 by actuating the invitation link or otherwise, portal 144 may render a popup requesting that the patient enrolls in RPM. Portal 144 may provide various options to the patient, such as options to select "Enroll" or select "I do not want to enroll". If the patient selects "I do not want to enroll", the healthcare provider receives a notification that the patient has denied the invitation to enroll in RPM. If the patient does not answer the invitation within a given time frame, they will receive an email and push notification reminder on the patient portal 112. In the event that the patient selects the "I do not want to enroll" option, for example, portal 144 may render reasons on why they should enroll in RPM. The reasons are customizable by the healthcare provider using the healthcare provider portal 112.

In response to selecting to enroll in RPM, portal 144 may prompt the patient to complete various fields, such as full name, date of birth, and phone number. Portal 144 may prompt the patient to agree to consent statements. Portal 144 may prompt the patient to agree that their provider has ordered the RPM for the reason the provider has given and voluntarily give their informed consent to enroll in and participate in the RPM program with the ordering provider. Portal 144 may prompt the patient to agree to a second statement accepting the terms of use. Each signature may be, for example, an e-signature. Once the patient has completed the consent forms, the RPM enrollment is complete. The patient's RPM status may be changed to "Enrolled." The healthcare provider may receive an email and/or a notification on the healthcare provider portal 112 that the patient has enrolled.

Once the patient is enrolled in RPM, the patient's disparate source 160 may send data transmissions, including health data, to central system 100. The sensor 160 may sense, track, and measure the health data of the patient. Data transmission application 164 may extract/pull the health data from sensor 162. For example, data transmission application 164 may extract/pull the health data every 24 hours. Alternatively, the sensor 160 may push the health data to data transmission application 164 continuously or periodically. Data transmission application 164 may form a health dataset from the health data. The health dataset may be transmitted to central system 100 using the data transmission application 164. In an embodiment, data transmission application 164 may automatically transmit the health dataset to central system 100 after collecting a specified amount of health data. Additionally or alternatively, data transmission application 164 may transmit the health dataset to central system 100 upon request by either the patient or central system 100.

API 106 may receive the data transmission from the data transmission application 164. Each of the data transmissions may include one or more time stamps. In embodiments, API 106 may receive health datasets from multiple different disparate sources of the same patient and/or from multiple different disparate sources of various patients. In some embodiments, API 106 may receive multiple health datasets from the same disparate source 160 corresponding to the single patient.

Syncing engine 101 may determine whether the health data is in a correct format. For example, the health data may be received in JavaScript Object Notation (JSON) data-interchange format or eXtensible Markup Language (XML) format. Syncing engine 101 may determine whether the JSON format is acceptable by database 148. In the event the health data is not in the correct format, syncing engine 101 may normalize the data into a format accepted by database 148. The healthcare data may include a disparate source ID from which the healthcare data was transmitted. Syncing engine 101 may determine the patient associated with the healthcare data using the disparate source ID. For example, syncing engine 101 may correlate the disparate source ID in the healthcare data with the disparate source ID of disparate source 160 tied to the patient. Reimbursement engine 102 may store the healthcare data in database 148 such that it is correlated to the patient record(s).

Syncing engine 101 may determine a date and time for the healthcare data from disparate source 160 based on the timestamp(s). The timestamp(s) may be generated when the data is generated, collected, or received by the disparate source and/or at the time disparate source 160 first attempted to transmit the data transmission. The healthcare data may be stored in database 148 based on the timestamp and the disparate source ID. In this way, sequential data collected continuously or periodically by a disparate source but transmitted asynchronously to a central location can be ordered properly when combined with other sequential data received at the central location from other disparate sources.

Reimbursement engine 102 may determine whether the healthcare provider is eligible for any reimbursement based on the received healthcare data. For example, in response to receiving data transmissions on a minimum threshold number of days within a given time window, for a first time, reimbursement engine 102 may determine that the healthcare provider is eligible for the set up reimbursement.

Reimbursement engine 102 may also track of frequency and amount of days of data transmissions from the patient. Reimbursement engine 102 may determine the healthcare provider is eligible for the data transmission reimbursement in response to determining there have been a minimum number of days of data transmissions for a patient in a specified time window and after a specified amount of days after the previous data transmission reimbursement eligibility was triggered or a specified amount of days after the date of enrollment.

Reimbursement engine 102 may also determine whether a healthcare provider is eligible for treatment reimbursement. For example, a healthcare provider may use the healthcare provider portal 112 to confirm that healthcare has been provided for a certain amount of time. For example, the healthcare provider may confirm that 20 minutes or more of clinical staff/physician/other qualified healthcare professional time in a calendar month have been provided. Furthermore, reimbursement engine 102 may confirm that data transmissions have been received for a minimum threshold number of days within a given time window and after a specified number of days have passed since the last triggered data transmission reimbursement eligibility or since the date of enrollment. In response to receiving the confirmation and that data transmissions have been received on a minimum threshold number of days within a given time window and after a specified number of days have passed since the last triggered data transmission reimbursement eligibility, or since the date of enrollment, reimbursement engine 102 may determine that the healthcare provider is eligible for treatment reimbursement for that patient.

Reimbursement engine 102 may forward all the received transmission data to portal management engine 104. Portal management engine 104 may render graphical user interfaces ("GUIs") for the healthcare provider portal 112 and portal 144. For example, portal management engine 104 may generate and render a data transmission GUI on the healthcare provider portal 112.

Furthermore, portal management engine 104 may generate and render a data transmission alert box. The data transmission alert box may include a list of patients that have not been transmitting data transmissions. For example, once a given amount of time passes without receiving any data transmission from a patient, the patient is added to the list. The list includes the patient's name and the number of days without transmitting a data transmission. The number of days will continue to increase in the event the patient fails to provide data transmissions.

This list may be configured to show patient(s), for example, from the least days without a data transmission to the highest days without data transmissions. A healthcare provider may filter the list, for example, based on a number of days without a data transmission. For example, the list may be filtered by name, by 3-5 days without a data transmission, 5-10 days without a data transmission, 10-30 days without a data transmission, >30 days without a data transmission, and so on. Additionally, an activity may be triggered when there have been no data transmissions from a patient in a given period of time, such that the healthcare provider is prompted to contact the patient.

Portal management engine 104 may also generate and render an eligibility report box. The eligibility report box may include all the eligibility reports for reimbursements for all patients. The previous month's eligibility report may be closed at the end of the day of the last day of the month and then may be ready to review and submit. The current eligibility progress may be viewed by clicking "View Progress". When clicking "View Progress," a popup may appear with all the list of patients enrolled in RPM and show which type of eligibility they are eligible for so far.

Portal management engine 104 may also generate and render a business trends GUI. The business trends GUI may include a graph of the number of patients enrolled in RPM and a graph of the data transmission index of the patients.

In an embodiment, reimbursement engine 102 may also determine whether a patient's data transmissions, including their health data, include a value corresponding to the patient's health, included in at least one of the received health datasets, that is passed a threshold level. For example, reimbursement engine 102 may determine whether a patient's body fat level is beyond a certain threshold, their heart rate is higher than a specified amount, their blood sugar level is higher than a threshold amount, and/or the like. Reimbursement engine 102 may generate and render an alert indicating the health data that should be brought to the healthcare provider's engine on the healthcare provider portal 112.

Figure 2:
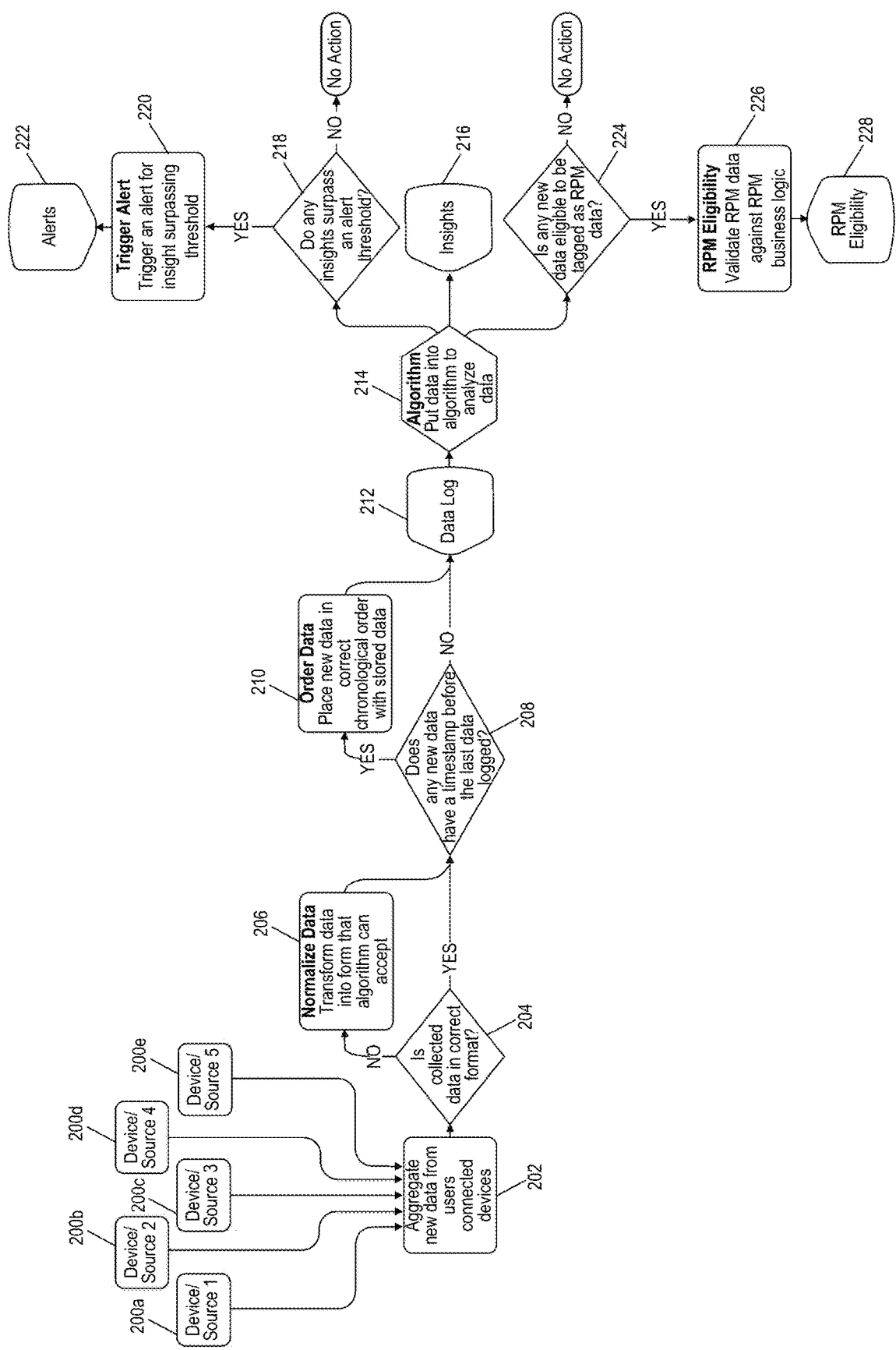
FIG. 2 illustrates data flow in a process for determining reimbursement eligibility according to an example embodiment.

FIG. 2 illustrates data flow in a process for determining reimbursement eligibility according to an example embodiment. In an embodiment, disparate sources 200a-e may transmit data transmissions, including data. The data may be patient health datasets. Each disparate source 200a-e may be associated with a different patient. The disparate sources 200a-e may be data collection devices. As an example, the data collection device may be a smartwatch or other smart device configured to capture patient health data. The health data may include, for example, weight, blood pressure, pulse oximetry, respiratory flow rate, and/or the like. The data transmissions may be transmitted to a central system using an existing transmission protocol, such as a JSON payload.

In operation 202, the central system may aggregate the health data sets from the disparate sources 200a-e. The central system may correlate the patient to each health dataset based on a device id of disparate source 200a-e, included in the data transmission. In addition, the central system may validate whether or not data transmitted by the disparate sources has already been previously collected by checking the health data's associated metadata so as not to transmit duplicate data.

In operation 204, the central system may determine whether the health datasets are correctly formatted. For example, as described above, the health datasets may be received by the central system in one format, such as a JSON payload or a XML, format. The central system may determine whether to format the health datasets into a different format, such as a different JSON format, so that the health datasets may be stored in a database. The central system may consolidate the health datasets for storage. For example, health datasets may include heart rates for a patient throughout a period of time. The central system may determine the resting heart rate for the day based on the various heart rates. In another example, health datasets may include various values for heart rate variability. The central system may filter out any heart rate variability that is less than a specified threshold.

In operation 206, in response to determining that the health datasets are not formatted correctly, the central system may normalize the data. As described above, the central system may format the data to a different JSON format so that the health datasets may be stored in a database. Additionally, the central system may consolidate data such as determining a resting heart rate based on the various heart rates received from the disparate source.

In operation 208, in response to normalizing the data or in response to determining that the health datasets are formatted correctly, the central system may determine whether the health datasets include timestamps that are earlier than the timestamp of the last data logged. The timestamps may correlate to a date and time when the data was generated, collected, or received by the disparate source or when the disparate source first attempted to transmit the data transmission. If a timestamp corresponding to the normalized data from operation 208 is later than a timestamp associated with the last known data that has already been logged by the central system, then the normalized data from operation 208 is simply added to the end of the data log as the method proceeds to operation 212. However, if the timestamp corresponding to the normalized data from operation 208 is earlier than a timestamp associated with the last known data that has already been logged by the central system, that means that the new data corresponds to an earlier time, even though it was received later. In such a case, the method proceeds to operation 210 prior to operation 212.

In operation 210, in response to determining that there is a timestamp associated with the health datasets, the central system may sort the health datasets (or the data transmissions, including the health datasets) in chronological order using the timestamp. The sorted health datasets may provide a more accurate reflection of the progression of the health data over a given time period, compared to the data logged as it is received from each of the disparate sources. For example, in the event, a disparate source intends to transmit five data transmissions on five different days, but the central system receives all five data transmissions on a single day, the sorted health datasets may account for each day the disparate source obtained and/or attempted to transmit the data. If the health datasets were to remain unsorted, this may lead the central system to incorrectly process the health datasets. Processing inaccurate data may cause inefficiencies in the system and may cause system failures or incorrect diagnoses by machine learning tools used to process data in operations 214-222 and 224-228. The sorted health datasets may provide a more accurate indication of when the health datasets were captured and transmitted. Accurate data may be prepared for further processing.

Furthermore, sorted health datasets may be used to determine reimbursement eligibility. For example, the central system may determine whether patient data exists for a minimum number of days in a specified time window, using the sorted health datasets. In an embodiment, the health datasets may be stored in a database and then sorted.

In operation 212, the central system may generate a data log using the health datasets.

In operation 214, the central system may process the health datasets of all the patients. For example, the central system may identify all the health datasets received for a particular patient. The system may use the health datasets for the particular patient to performing calculations associated with the health of the patient. As an example, health datasets may include body weight and height. The central system may use body weight and height to calculate a body mass index (BMI). In another example, health datasets may include the patient's physical activity, fitness, and body composition. The central system may use the patient's activity, fitness, and body composition to generate an activity benefit percentage (i.e., an index of benefit patient obtains from the amount of activity they perform). As another example, the central system may generate a fitness age based on an estimated VO2max, received in the health dataset.

In operation 216, the central system may determine whether there are any insights into the patient's health using health datasets. For example, the insights can be a change in weight, average heart rate, blood pressure, and/or the like. Such insights may be obtained via a machine learning model trained to identify health issues based on a progression of patient activity and data. Such machine learning models used to generate insights into a patient's health and/or diagnose or predict health issues based on certain measurable parameters are known to those skilled in the art and not further described here.

In operation 218, the central system may determine whether any value or insight in the health dataset was outside a threshold. For example, the central system may determine whether a patient's average heart rate is higher than a threshold amount or the blood pressure is higher or lower than a threshold amount. In another example, the central system may determine that a mood state of a patient is more negative than a threshold level.

In operation 220, in response to determining that an insight or value in the health dataset is outside a threshold, the central system may trigger an alert to be transmitted to the healthcare provider portal.

In operation 222, the alerts may be transmitted to the healthcare provider portal. The alert may include the reason for the alert, including the insight or value in the health dataset that was outside of a threshold amount.

In operation 224, the central system may determine whether, in response to receiving the latest health dataset for a patient, reimbursement eligibility is triggered.

In operation 226, in response to determining that reimbursement eligibility is triggered, the central system may validate the health dataset for the patient to determine which type of reimbursement eligibility is triggered. The types of data reimbursement may include, for example, a set up data reimbursement, a data transmission reimbursement, or a treatment reimbursement. For example, the central system may determine that the set up reimbursement eligibility is triggered in response to receiving data transmissions on a minimum threshold number of days within a given time window, for the first time.

The central system may determine that the data transmission reimbursement is triggered based on the most recently received health dataset if the central system identifies that a minimum number of days with logged data within a specified time window has been met, and a specified amount of days has passed since the last data transmission reimbursement or date of enrollment in RPM by the patient. The number of days with logged data may depend on when the disparate source generated, collected, or received the data or first attempted to send the health dataset, irrespective of when the central system actually received the health dataset. As an example, as described above, the disparate source may attempt to transmit a data transmission for five different days, but the patient may be outside of network connectivity areas for five days. Therefore, when the disparate source regains network connectivity, the disparate source may complete the transmitting of the five data transmissions all in one day. When synced according to an embodiment of the invention, the five data transmissions may be counted as five days' worth of data transmissions for the purposes of the data transmission reimbursement, rather than a single day's worth of data transmission based only on the date of receipt.

A healthcare provider may be eligible for a treatment reimbursement based on remote physiologic monitoring treatment management services over a period of time with the patient/caregiver and receiving a minimum threshold number of days within a given time window and after a specified number of days have passed since the last triggered data transmission reimbursement eligibility or since the date of enrollment. The treatment reimbursement may require interactive communication with the patient/caregiver during a period of time for more than a threshold amount of time (e.g., 20 minutes in a calendar month).

In operation 224, the central system may trigger reimbursement eligibility for patients for the relevant reimbursement types.

Figure 3:
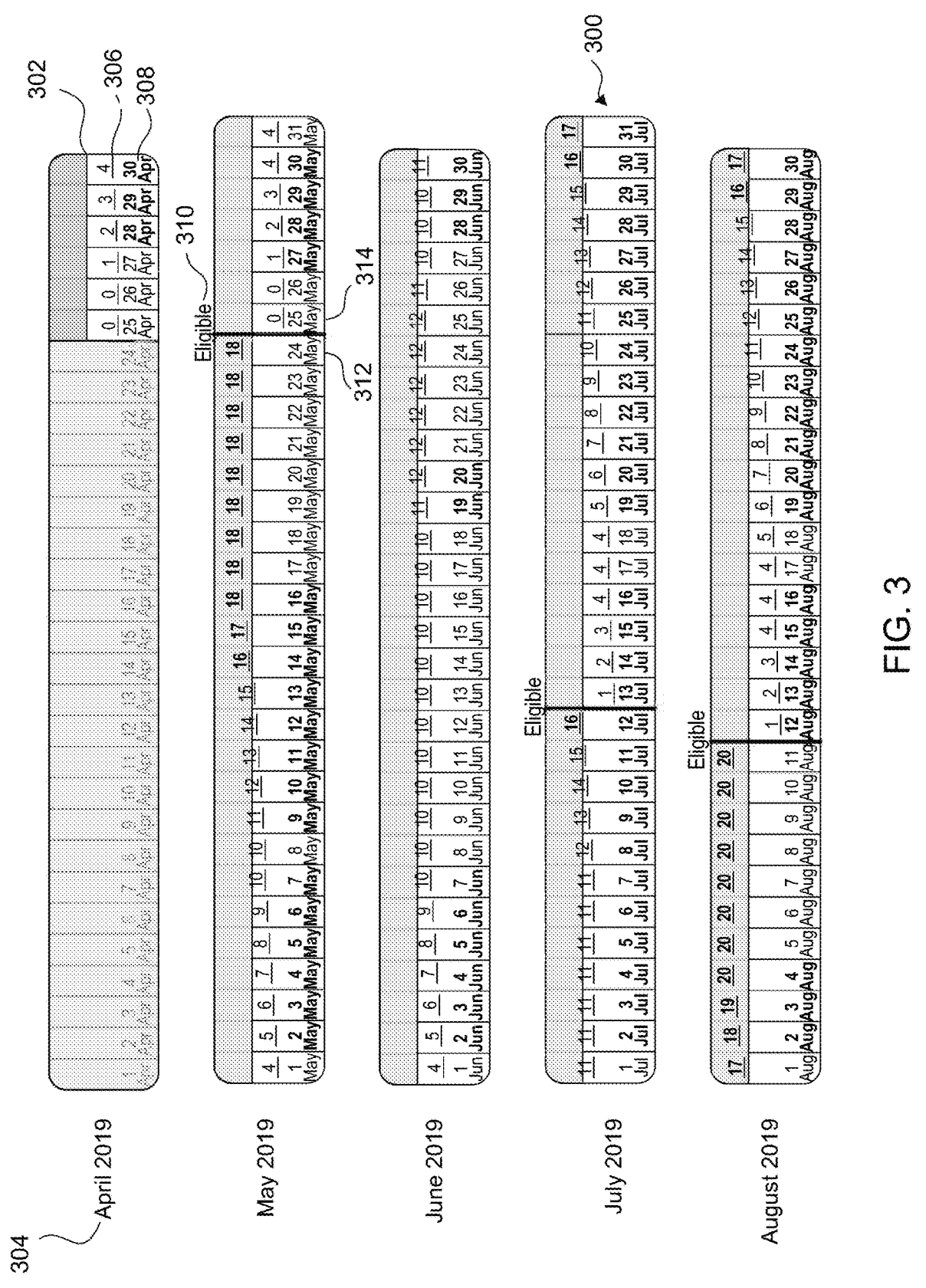

FIG. 3 is an example data transmission log 300 illustrating a visual representation of a patient's data transmissions over several months. In an embodiment, data transmission log 300 may not be rendered on the GUI for the user. Alternatively, in an embodiment, data transmission log 300 may be rendered on a GUI for the user. Data transmission log 300 may include sections 302 for each day of a month 304. Sections for the days prior to a patient's enrollment may be grayed out or otherwise visually diminished. The sections after the patient's enrollment may indicate the day of the month and the month. Sections 302 may also include a numerical amount 306 indicating the total number of days within a given time period on which data was logged. A horizontal line may correspond to numerical amount 306. As the numerical amount increases, the position of the numerical amount and horizontal line may be positioned higher in section 302 as compared to previous section 302. An area at the top of section 302 may be visually different from the rest of the section. The visually different part of the section may correspond with a minimum number of days of logged data required for data transmission reimbursement. For example, when the numerical amount of the total days of logged data is less than the minimum number of days of logged data required, the numerical amount and horizontal line may be positioned below the visually different area of section 302. Alternatively, when the numerical amount of the total days of data transmission is greater than the minimum number of days of data transmissions required, the numerical amount and horizontal line may be included within the visually different area of section 302. As an example, the day of the month and the month may be gray or otherwise visually diminished to signify not receiving data corresponding to that date. In comparison, the day of the month and the month may be green or otherwise visually highlighted to signify receiving data corresponding to that date.

In response to determining that the patient has logged data on a minimum number of days within the specified time window and after the specified amount of days since the date of the last triggered reimbursement eligibility for the patient or the date of reimbursement enrollment, the healthcare provider may become eligible for the data transmission reimbursement for that patient. In response to the healthcare provider becoming eligible for the data transmission reimbursement, data transmission log 300 may include a visual indicator 310 indicating eligibility. Visual indicator 310 may be, for example, a vertical line positioned in between section 312 corresponding to the date after the healthcare provider became eligible for the data transmission reimbursement and section 314 corresponding to date directly after the date corresponding to section 312. The word "Eligible" or another highlighting identifier may be positioned above the vertical line.

As a non-limiting example, a healthcare provider may be eligible for data transmission reimbursement after 16 days of data logged within a 30 day period and after 30 days from when the data transmission reimbursement was triggered or 30 days after the enrollment date. In the example illustrated in FIG. 3, a patient may enroll in RPM on April 25. Data transmission log 300 may start tracking data transmissions from the patient on April 25 after enrollment. The first health data from a patient may be timestamped on April 27. Section 300 corresponding to April 27 includes a "1" for 1 day of the data transmission received, and the "27" and "April" may be green to indicate a received data transmission. Data transmissions for the patient may have timestamps of April 27 through April 30, totaling four data transmissions. The numerical amount of "4" may be included in the section corresponding to April 30. No data transmissions that have a timestamp of May 1 are received. The total number of days with data transmissions is still four. Therefore, a numerical amount of "4" is included in the section corresponding to May 1. The date, "1" and "May" is gray, to indicate that no data transmission has been received that day.

On May 14, the patient reaches 16 days of data transmissions within the past 30 days. However, as 30 days have not passed since the enrollment date, the data reimbursement eligibility is not yet triggered. Once 30 days have passed since the enrollment date of April 25, on May 24, the data reimbursement transmission eligibility is triggered. Once data transmission reimbursement eligibility is triggered, the total amount of days of data transmissions is reset to 0. Therefore, as no data transmission has a timestamp of May 25, and as the clock restarts on May 25, the total amount of days with data logged is shown as 0 on May 25.

Within the next 30 day span from May 25 to June 23, the patient does not have 16 days of data logged. In light of this, the start of the 30-day time frame (to receive 16 days of data transmissions) shifts by one day as each day passes beyond the 30 days. For example, on June 24, the start of the 30-day time frame is shifted to change from May 25 to May 26. On June 25, the 30-day time frame is shifted to start from May 27, and on June 26, the 30-day time frame is shifted to start from May 28. As data transmissions have not been received having timestamps of June 25, 26, and 27, the total number of days of logged data decreases for days past June 25 because the data transmission on May 27 is no longer counted. Data transmission reimbursement eligibility is triggered again on July 12, after receiving data transmissions for 16 days in a 30-day window after at least 30 days have passed since the last triggered reimbursement eligibility of May 24. Data transmission eligibility is triggered again on August 11 after receiving data transmissions for 16 days in a 30-day window and after at least 30 days have passed since the last triggered reimbursement eligibility of July 12.

Figure 4:
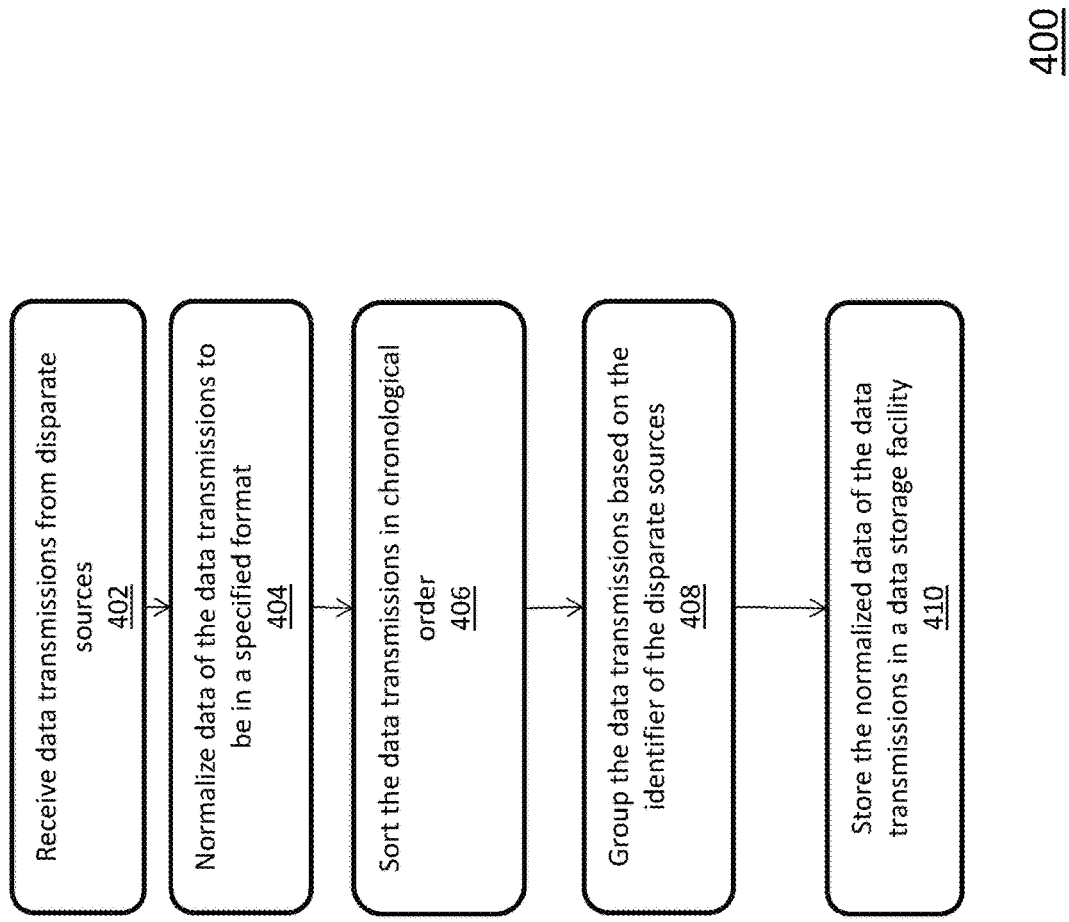
FIGS. 4-5 are flowcharts illustrating a process for asynchronously syncing the received sequential data from disparate sources according to an example embodiment

FIG. 4 is a flowchart illustrating a process 400 implemented by a system for syncing asynchronously received sequential data received from disparate sources, as discussed above. It is to be appreciated the operations may occur in a different order, and some operations may not be performed.

In operation 402, a central system may receive data transmissions from disparate sources. Each data transmission may include one or more timestamps corresponding to when a data element was generated, collected, or received by the disparate source, and/or a data transmission was attempted to be transmitted by a disparate source, along with an identifier of the disparate source.

In operation 404, the central system may normalize data of the data transmissions to be in a specified format. For example, the data may be received in a different format than the specified format.

In operation 406, the central system may sort the data in the data transmissions in chronological order based on the timestamp of each of the data transmissions.

In operation 408, the central system may group the data transmissions based on the identifier of the disparate sources.

In operation 410, the central system may store the normalized data of the data transmissions in a data storage component or facility based on the identifier of the disparate sources and the sorted order of the data transmissions.

Figure 5:
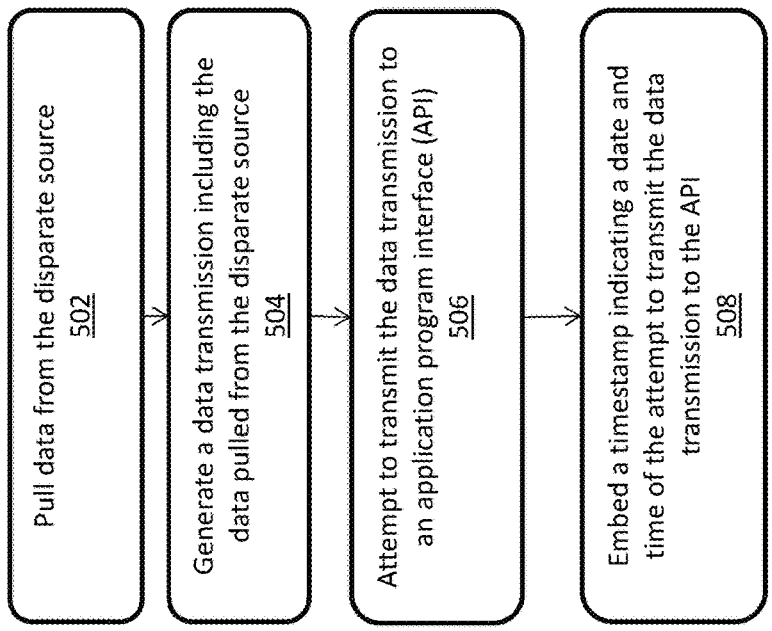

FIG. 5 is a flowchart illustrating a process 500 implemented by a system for syncing asynchronously received sequential data received from disparate sources, as discussed above. It is to be appreciated the operations may occur in a different order, and some operations may not be performed.

In operation 502, an application executing on a disparate source may obtain data from a sensor on or connected to the disparate source or data which is otherwise stored on the disparate source.

In operation 504, the application may generate a data transmission, including the data.

In operation 506, the application may transmit or attempt to transmit the data transmission to an application program interface (API).

In operation 508, the application may embed a timestamp indicating a date and time of the attempt to transmit the data transmission to the API and/or a date and time corresponding to the date and time the data was generated, collected, or received by the disparate source.

Figure 6:
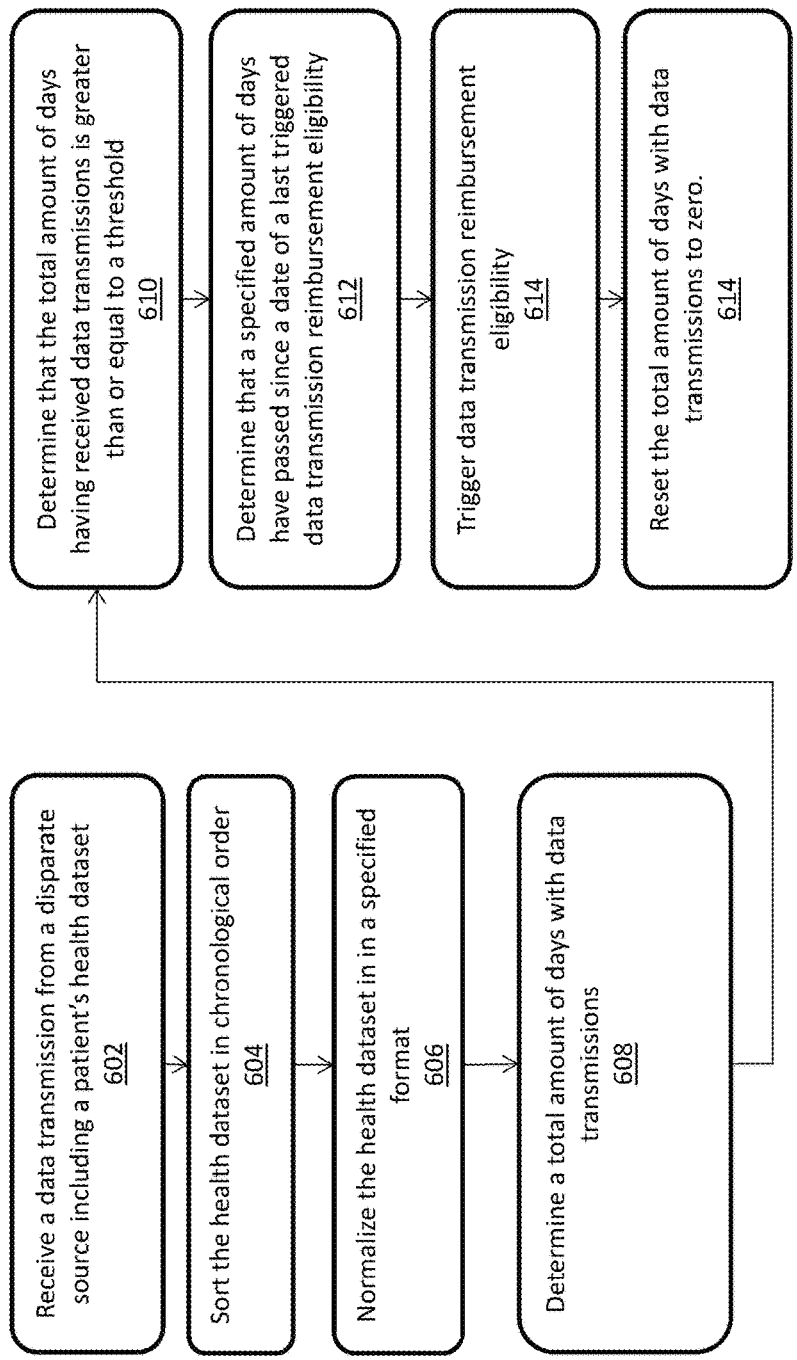
FIGS. 6-7 are flowcharts illustrating processes implemented for determining reimbursement eligibility according to an example embodiment.

FIG. 6 is a flowchart illustrating a process 600 implemented for determining reimbursement eligibility, as discussed above. It is to be appreciated the operations may occur in a different order, and some operations may not be performed.

In operation 602, a central system may receive a data transmission from a disparate source, including a patient's health dataset on a given day. The health dataset may include one or more timestamps.

In operation 604, the central system may sort data in the health dataset in chronological order based on the timestamp(s) of the health dataset, among other received health datasets.

In operation 606, the central system may normalize the health dataset in a specified format.

In operation 608, the central system may determine a total number of days with data logged for the patient, including all previous days with logged data within the specified time window and the given day, based on the sorted health datasets;

In operation 610, the central system may determine that the total amount of days having logged data is greater than or equal to a threshold amount of days within the specified time window.

In operation 612, the central system may determine that a specified amount of days have passed since a date of a last triggered data transmission reimbursement eligibility for the patient or since the date of reimbursement enrollment for the patient.

In operation 614, the central system may trigger data transmission reimbursement eligibility. The central system may also trigger set up reimbursement eligibility in response to receiving data transmissions on a minimum threshold number of days within a given time window, for a first time.

Furthermore, the central system may also trigger the treatment reimbursement eligibility in response to receiving confirmation that a healthcare professional has provided more than a threshold amount of healthcare time to the patient and receiving a minimum threshold number of days within a given time window and after a specified number of days have passed since the last triggered data transmission reimbursement eligibility or since the date of enrollment.

In operation 616, the central system may reset the total number of days with logged data to zero.

Figure 7:
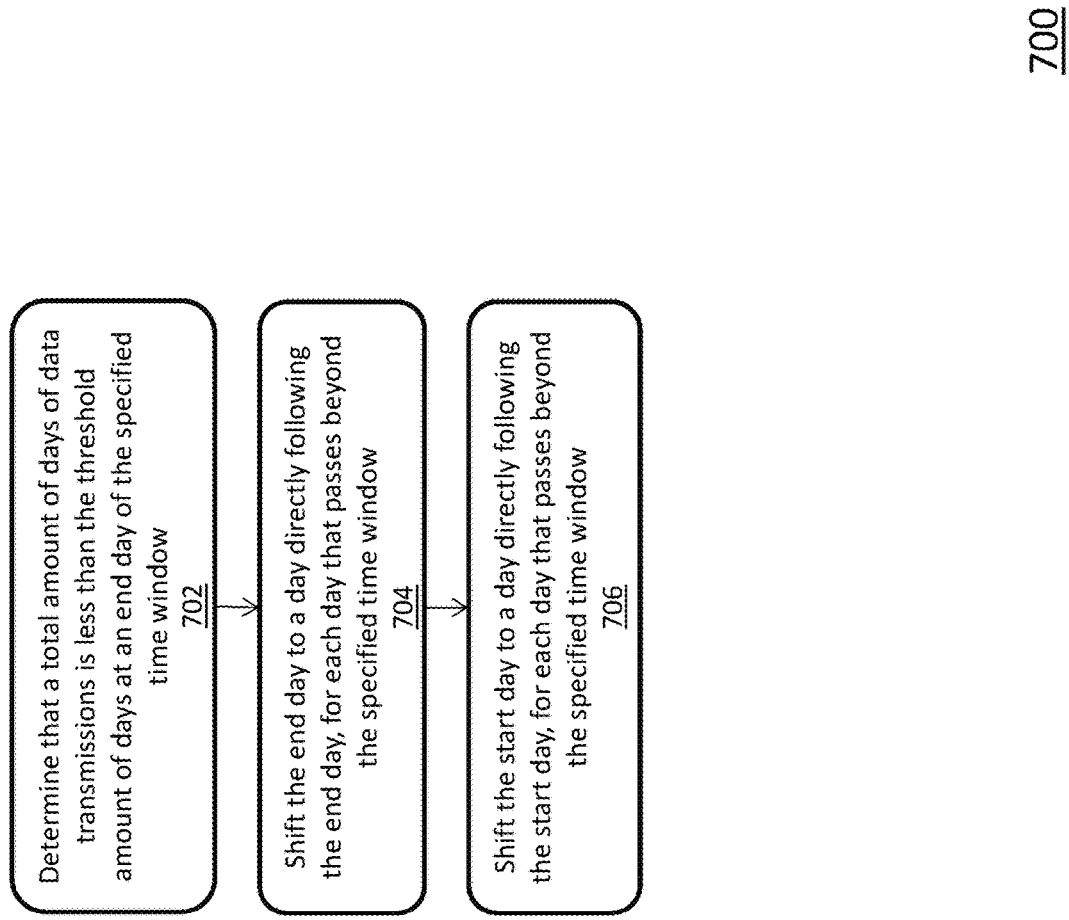

FIG. 7 is a flowchart illustrating a process 700 for determining reimbursement eligibility, as discussed above. It is to be appreciated the operations may occur in a different order, and some operations may not be performed.

In operation 702, the central system determines that a total amount of days of logged data is less than the threshold amount of days at an end day of a specified time window.

In operation 704, the central system shifts the end day to a day directly following the previous end day for each day that passes beyond the specified time window.

In operation 706, the central system shifts the start day to a day directly following the previous start day for each day that passes beyond the specified time window.

Figure 8:
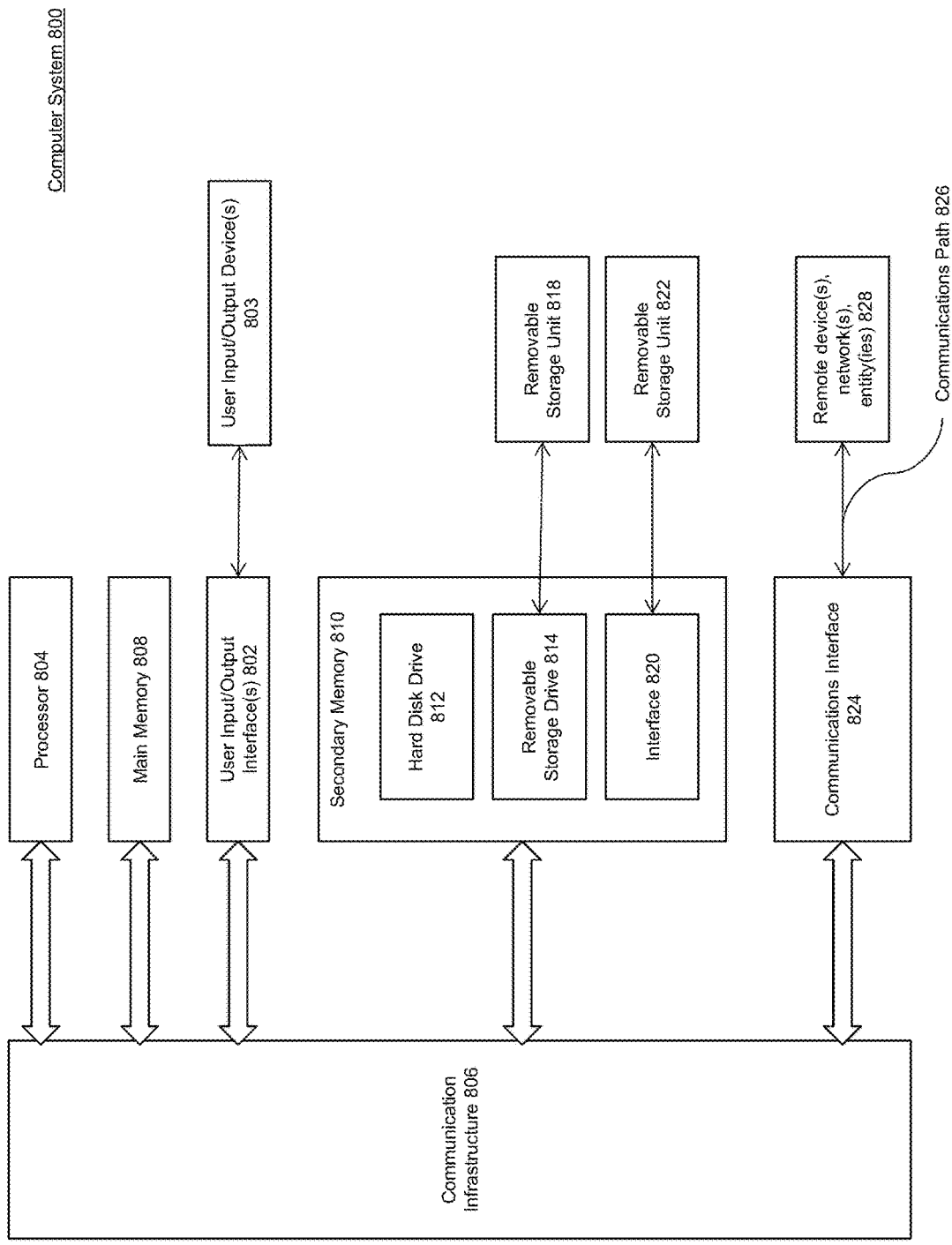
FIG. 8 is a block diagram of example components of a computing system according to an embodiment according to an example embodiment.

FIG. 8 is a block diagram of example components of a computer system 800. One or more computer systems 800 may be used, for example, to implement any of the embodiments discussed herein, as well as combinations and subcombinations thereof. Computer system 800 may include one or more processors (also called central processing units, or CPUs), such as a processor 804. Processor 804 may be connected to a communication infrastructure or bus 806.

Computer system 800 may also include user input/output device(s) 803, such as monitors, keyboards, pointing devices, etc., which may communicate with communication infrastructure 806 through user input/output interface(s) 802.

One or more of processors 804 may be a graphics processing unit (GPU). In an embodiment, a GPU may be a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 800 may also include a main or primary memory 808, such as random access memory (RAM). Main memory 808 may include one or more levels of cache. Main memory 808 may have stored therein control logic (i.e., computer software) and/or data.

Computer system 800 may also include one or more secondary storage devices or memory 810. Secondary memory 810 may include, for example, a hard disk drive 812 and/or a removable storage device or drive 814.

Removable storage drive 814 may interact with a removable storage unit 818. Removable storage unit 818 may include a computer usable or readable storage device having stored thereon computer software (control logic) and/or data. Removable storage unit 818 may be program cartridge and cartridge interface (such as that found in video game devices), a removable memory chip (such as an EPROM or PROM) and associated socket, a memory stick and USB port, a memory card and associated memory card slot, and/or any other removable storage unit and associated interface. Removable storage drive 814 may read from and/or write to removable storage unit 818.

Secondary memory 810 may include other means, devices, components, instrumentalities or other approaches for allowing computer programs and/or other instructions and/or data to be accessed by computer system 800. Such means, devices, components, instrumentalities or other approaches may include, for example, a removable storage unit 822 and an interface 820. Examples of the removable storage unit 822 and the interface 820 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 800 may further include a communication or network interface 824. Communication interface 824 may enable computer system 800 to communicate and interact with any combination of external devices, external networks, external entities, etc. (individually and collectively referenced by reference number 828). For example, communication interface 824 may allow computer system 800 to communicate with external or remote devices 828 over communications path 826, which may be wired and/or wireless (or a combination thereof), and which may include any combination of LANs, WANs, the Internet, etc. Control logic and/or data may be transmitted to and from computer system 800 via communication path 826.

Computer system 800 may also be any of a personal digital assistant (PDA), desktop workstation, laptop or notebook computer, netbook, tablet, smart phone, smart watch or other wearable, appliance, part of the Internet-of-Things, and/or embedded system, to name a few non-limiting examples, or any combination thereof.

Computer system 800 may be a client or server, accessing or hosting any applications and/or data through any delivery paradigm, including but not limited to remote or distributed cloud computing solutions; local or on-premises software ("on-premise" cloud-based solutions); "as a service" models (e.g., content as a service (CaaS), digital content as a service (DCaaS), software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), etc.); and/or a hybrid model including any combination of the foregoing examples or other services or delivery paradigms.

Any applicable data structures, file formats, and schemas in computer system 800 may be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats or schemas may be used, either exclusively or in combination with known or open standards.

In some embodiments, a tangible, non-transitory apparatus or article of manufacture comprising a tangible, non-transitory computer useable or readable medium having control logic (software) stored thereon may also be referred to herein as a computer program product or program storage device. This includes, but is not limited to, computer system 800, main memory 808, secondary memory 810, and removable storage units 818 and 822, as well as tangible articles of manufacture embodying any combination of the foregoing. Such control logic, when executed by one or more data processing devices (such as computer system 800), may cause such data processing devices to operate as described herein.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries may be defined so long as the specified functions and relationships thereof are appropriately performed.

The foregoing description of the specific embodiments will so fully reveal the general nature of the invention that others may, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method for syncing asynchronously received sequential data transmissions from disparate sources, the method comprising:
    receiving, by one or more computing devices, a plurality of data transmissions from a plurality of disparate sources, each data transmission including a first timestamp generated by a respective disparate source of the plurality of disparate sources and an identifier of the respective disparate source, wherein the first timestamp corresponds to a date and time that the respective disparate source attempted to transmit the data transmission;
    assigning an identifier to each of the plurality of data transmissions based on when each of the plurality of data transmissions was received by the one or more computing devices, wherein at least two or more of the plurality of data transmission were received in a different order than the date and time indicated by the first timestamp of each of the plurality of data transmissions;
    reordering the plurality of data transmissions in accordance with the first timestamp, wherein the reordered plurality of data transmissions are reordered in accordance with when each of the plurality of data transmissions was attempted to be transmitted rather than when each of the plurality of data transmissions was received;
    determining that each data transmission includes at least one entry including a second timestamp indicating when the at least one entry was generated, collected, or received by the respective disparate source, wherein the second timestamp is prior to the first timestamp;
    normalizing, by the one or more computing devices, data of the data transmissions to be in a specified format;
    sorting, by the one or more computing devices, the normalized data of the data transmissions in chronological order based on one of the first timestamp or the second timestamp included in each data transmission;
    grouping, by the one or more computing devices, the normalized data based on the identifiers of the disparate sources; and
    storing, by the one or more computing devices, the normalized data of the data transmissions in a data storage facility based on the identifiers of the disparate sources and the sorted order of the normalized data.

2. The method of claim 1, further comprising
    obtaining, by the one or more computing devices, data from at least one of the disparate sources, using an application executing on the at least one disparate source.

3. The method of claim 1, wherein a date in a timestamp of at least one data transmission is different from a date the at least one data transmission was received.

4. The method of claim 1, wherein the data in at least one data transmission is received in a different format from the specified format.

5. The method of claim 1, wherein the disparate source is a data collection device configured to track and collect sequential health datasets of a user.

6. The method of claim 1, further comprising
    triggering, by the one or more computing devices, an action based on dates included in timestamps of each of the data transmissions and the identifier of each of the plurality of data transmissions.

7. A system for syncing asynchronously received sequential data transmissions from disparate sources, the system comprising:
    a memory; and
    a processor coupled to a memory, the processor configured to:
        receive a plurality of data transmissions from a plurality of disparate sources, each data transmission including a first timestamp generated by a respective disparate source of the plurality of disparate sources and an identifier of the respective disparate source, wherein the first timestamp corresponds to a date and time that the respective disparate source attempted to transmit the data transmission;
        assign an identifier to each of the plurality of data transmissions based on when each of the plurality of data transmissions was received by the processor, wherein at least two or more of the plurality of data transmissions were received in a different order than the date and time indicated by the first timestamp of each of the plurality of data transmissions;
        reorder the plurality of data transmissions in accordance with the first timestamp, wherein the reordered plurality of data transmissions are reordered in accordance with when each of the plurality of data transmissions was attempted to be transmitted rather than when each of the plurality of data transmissions was received;
        determine that each data transmission includes at least one entry including a second timestamp indicating when the at least one entry was generated, collected, or received by the respective disparate source, wherein the second timestamp is prior to the first timestamp;

normalize data of the data transmissions to be in a specified format;

sort the normalized data of the data transmissions in chronological order based on one of the first timestamp or the second timestamp included in each data transmission;

group the normalized data based on the identifiers of the disparate sources; and store the normalized data of the data transmissions in a data storage facility based on the identifiers of the disparate sources and the sorted order of the normalized data.

8. The system of claim 7, wherein the processor is further configured to:

obtain data from at least one of the disparate sources, using an application executing on the at least one disparate source.

9. The system of claim 7, wherein a date in a timestamp in at least one data transmission is different from a date the at least one data transmission was received.

10. The system of claim 7, wherein the data in at least one data transmission is received in a different format from the specified format.

11. The system of claim 7, wherein the disparate source is a data collection device configured to track and collect sequential health datasets of a user.

12. The system of claim 7, wherein the processor is further configured to: trigger an action based on dates included in timestamps of each of the data transmissions and the identifier of each of the plurality of data transmissions.

13. A non-transitory computer-readable medium having instructions stored thereon that, when executed by at least one computing device, cause the at least one computing device to perform operations comprising:

receiving a plurality of data transmissions from a plurality of disparate sources, each data transmission including a first timestamp generated by a respective disparate source of the plurality of disparate sources and an identifier of the respective disparate source, wherein the first timestamp corresponds to a date and time that the respective disparate source attempted to transmit the data transmission;

assigning an identifier to each of the plurality of data transmissions based on when each of the plurality of data transmissions were received by the at least one computing device, wherein at least two or more of the plurality of data transmissions were received in a different order than the date and time indicated by the first timestamp of each of the plurality of data transmissions;

reordering the plurality of data transmissions in accordance with the first timestamp, wherein the reordered plurality of data transmissions are reordered in accordance with when each of the plurality of data transmission was attempted to be transmitted rather than when each of the plurality of data transmissions was received;

determining that each data transmission includes at least one entry including a second timestamp indicating when the at least one entry was generated, collected, or received by the respective disparate source, wherein the second timestamp is prior to the first timestamp;

normalizing data of the data transmissions to be in a specified format;

sorting the normalized data of the data transmissions in chronological order based on one of the first timestamp or the second timestamp included in each data transmission;

grouping the normalized data based on the identifiers of the disparate sources; and storing the normalized data of the data transmissions in a data storage facility based on the identifiers of the disparate sources and the sorted order of the normalized data.

14. The non-transitory computer-readable medium of claim 13, the operations further comprising:

obtaining data from at least one of the disparate sources, using an application executing on the at least one disparate source.

15. The non-transitory computer-readable medium of claim 14, wherein a date in a timestamp of at least one data transmission is different from a date of when the at least one data transmission was received.

16. The non-transitory computer-readable medium of claim 14, wherein the data in at least one data transmission is received in a different format from the specified format.

17. The non-transitory computer-readable medium of claim 14, wherein the disparate source is a data collection device configured to track and collect sequential health datasets of a user.

18. The method of claim 1, wherein each data transmission includes health data of a user obtained from a sensor communicatively coupled to the respective disparate source.

19. The method of claim 18, wherein the respective disparate source is configured to pull the health data from the sensor in accordance with a data pull schedule.

20. The method of claim 1, further comprising:

determining that a threshold period of time has passed since a most recent data transmission was received from one or more of the plurality of disparate sources, wherein the data transmissions comprise health data regarding a patient managed by a healthcare provider; and responsive to the determination that the threshold period of time has passed since the most recent data transmission was received from the one or more of the plurality of disparate sources, prompting the healthcare provider to contact the patient.

21. The method of claim 1, further comprising:

determining that a mood state of a patient is more negative than a threshold level; and responsive to the mood state of the patient being more negative than the threshold level, prompting the healthcare provider to contact the patient.

\* \* \* \* \*